US012478724B2

(12) United States Patent
Koenig et al.

(10) Patent No.: US 12,478,724 B2
(45) Date of Patent: Nov. 25, 2025

(54) TEMPERATURE MANAGEMENT SYSTEM FOR PATIENTS DURING STATIONARY AND MOBILE ECLS/ECMO THERAPY

(71) Applicant: Irasun GmbH, Munich (DE)

(72) Inventors: Fabian Koenig, Unterföhring (DE); Florian Altinger, Munich (DE)

(73) Assignee: IRASUN GMBH, Munich (DE)

( * ) Notice: Subject to any disclaimer, the term of this patent is extended or adjusted under 35 U.S.C. 154(b) by 1022 days.

(21) Appl. No.: 17/444,541

(22) Filed: Aug. 5, 2021

(65) Prior Publication Data

US 2022/0331503 A1 Oct. 20, 2022

(30) Foreign Application Priority Data

Apr. 19, 2021 (EP) .................................... 21169268

(51) Int. Cl.
*A61M 1/36* (2006.01)
*F04D 7/02* (2006.01)

(52) U.S. Cl.
CPC .......... *A61M 1/369* (2013.01); *A61M 1/3666* (2013.01); *F04D 7/02* (2013.01); *A61M 2205/123* (2013.01); *A61M 2205/15* (2013.01); *A61M 2205/3606* (2013.01); *A61M 2205/366* (2013.01)

(58) Field of Classification Search
CPC .... A61M 1/153; A61M 1/155; A61M 1/1562; A61M 1/1698; A61M 1/3623; A61M 1/3666; A61M 1/369; A61M 2205/123; A61M 2205/3368; A61M 2205/3606; A61M 2205/366; A61M 2205/15; A61M 2205/6045; F04D 7/02
See application file for complete search history.

(56) References Cited

U.S. PATENT DOCUMENTS

| | | | | |
|---|---|---|---|---|
| 5,770,149 | A | 6/1998 | Raible | |
| 2003/0045917 | A1* | 3/2003 | Noda | A61F 7/12 607/113 |
| 2003/0126910 | A1* | 7/2003 | Burbank | A61M 1/367 73/40 |
| 2007/0197951 | A1* | 8/2007 | Mannlein | A61M 5/44 604/6.13 |

(Continued)

FOREIGN PATENT DOCUMENTS

| | | | |
|---|---|---|---|
| DE | 102017217782 | A1 | 4/2019 |
| EP | 1371381 | A1 | 12/2003 |
| WO | 2017148984 | A1 | 9/2017 |

(Continued)

*Primary Examiner* — Kai H Weng
(74) *Attorney, Agent, or Firm* — McCoy Russell LLP

(57) ABSTRACT

The present disclosure relates to a system for temperature management for patients in stationary and mobile ECLS and/or ECMO therapy, with a disposable and a fluid circuit, wherein the disposable comprises a reservoir or bag provided with at least one supply line and a drain line, further comprising a pumping unit element as part of the disposable, by means of which liquid in the reservoir or bag can be pumped through the fluid circuit, wherein in the mounted state of the system all fluid-guiding parts of the system are completely encapsulated and separated from intracorporeal and extracorporeal blood circuit of the patient undergoing the ECLS and/or ECMO therapy.

18 Claims, 10 Drawing Sheets

(56) References Cited

U.S. PATENT DOCUMENTS

| | | | | |
|---|---|---|---|---|
| 2014/0172050 | A1 * | 6/2014 | Dabrowiak | A61F 7/12 607/106 |
| 2020/0276376 | A1 * | 9/2020 | Wolfgramm | F28D 7/0008 |

FOREIGN PATENT DOCUMENTS

| | | | |
|---|---|---|---|
| WO | 2018099593 | A1 | 6/2018 |
| WO | 2018140414 | A1 | 8/2018 |
| WO | 2020074357 | A1 | 4/2020 |
| WO | 2020081991 | A2 | 4/2020 |
| WO | WO-2020081995 | A2 * | 4/2020 |
| WO | 2020112902 | A1 | 6/2020 |
| WO | 2021137116 | A1 | 7/2021 |

* cited by examiner

TEMPERATURE MANAGEMENT SYSTEM FOR PATIENTS DURING STATIONARY AND MOBILE ECLS/ECMO THERAPY

CROSS REFERENCE TO RELATED APPLICATION

The present application claims priority to European Patent Application No. 21169268.6 filed on Apr. 19, 2021. The entire contents of the above-listed application is hereby incorporated by reference for all purposes.

TECHNICAL FIELD

This disclosure relates to a system for patient blood temperature management, applied for example to patients during stationary and mobile ECLS/ECMO therapy, an assembly comprising a system and a medical device and a method for operating a system for patient temperature management.

BACKGROUND

Circulatory diseases (which include heart disease and stroke) have remained the most common cause of death in the Western world. In Europe, more than 275,000 people per year suffer cardiac arrest outside of clinical settings. Even with immediate onset of conventional cardiopulmonary resuscitation (CPR), survival with no or minimal neurological damage is minimal. An alternative to conventional CPR is extracorporeal membrane oxygenation (ECMO). In addition, comprehensive treatment of patients is usually only possible in specialized centers. However, the stabilization of patients for transport is very difficult in most cases. Here as well, ECMO offers new alternatives.

Extracorporeal membrane oxygenation (ECMO) is a machine-based cardiovascular support that can support or completely replace both the pulmonary oxygenation of the blood as well as the pumping function of the heart. It represents a promising but also highly invasive therapy option, which was initially used purely as "ultima ratio" therapy. Low experience combined with a high-risk patient clientele resulted in high mortality rates. With increasing experience and improved medical devices and therapies, initial problems have been resolved and complication rates significantly reduced. Contraindications to the use of ECMO therapy—also known as Extra Corporeal Life Support (ECLS)—have been greatly reduced. ECMO therapy quickly spread to new fields of application and indications, and new therapeutic approaches were developed. In addition to resuscitation during cardiac arrest and treatment of respiratory failure, the ECMO therapy also provides a bridging solution (bridge to transplant, bridge to VAD (ventricular assist device)). Another important application is the ability to treat patients with cardiogenic shock or under resuscitation for transport to a specialized center to stabilize. In pediatrics, ECMO now also plays a central role, especially as it is often the only therapy option besides a VAD.

ECMO therapy is now an established intensive care therapy and is one of the standard procedures at cardiac surgery centers. The survival rate improved to an average of 68% in 2017, which is a great success given the high-risk clientele. The average survival of all ECMO patients from 1986 to 2006 was approximately 50%.

ECMO systems are known for example from U.S. Pat. No. 5,770,149A.

A central component of said systems are oxygenators. Oxygenators enrich the patient's blood with oxygen. By monitoring the blood flow and controlling the gas blender, it is always possible to ensure the optimal oxygen or carbon dioxide content in the blood.

Since the patient's blood is passed through long external tubes, it cools down significantly. The energy loss is so high that the body cannot compensate for it independently. In order to avoid lowering the body core temperature, it is necessary to induce heat energy into the patient. For this purpose, the oxygenators of the ECLS systems offer an integrated heat exchanger. In addition, if necessary, e.g. to reduce the oxygen consumption in the organism, the heat exchangers in the oxygenator are used to cool the patient.

Heat exchange oxygenators are known, for example, from EP1371381A1.

Controlling the patient blood temperature indirectly by use of a water cycle through the oxygenators heat exchanger is also utilized during the use of the heart-lung machine. Thus, devices already exist for this application. However, as these have to offer the option of cooling the patients in addition to the heating function, they are referred to as hypothermia devices. These have an open water tank and are with an overall weight of more than 100 kg not suitable for mobile use. Their intended use is purely in the temperature control of patients during cardio-surgical operations utilizing heart-lung machines.

Hypothermia devices are known for example from DE102017217782A1.

Current hypothermia devices on the market have the considerable and central disadvantage that they work with a water reservoir and fixed stationary pumps and tubes. A complete and clinically correct cleaning of the system is therefore extremely complex and highly difficult to carry out. Improperly performed cleaning of the system can lead to contamination in the immediate area. Because these systems are typically placed in the intensive care unit as close to the patient as possible, the risk to contaminate the patient must be considered.

While several compact, portable ECLS systems have been developed, a specialized temperature management device for that dedicated purpose and application has not yet been developed. Currently used temperature control devices connected to the heat exchanger of the oxygenator were originally developed to control the temperature of heating mats. In terms of safety, hygiene and practicability, these devices have significant shortcomings when combined with ECLS systems.

One major disadvantage of the existing ECLS devices is the extracorporeal flow of patient blood through tubing. The temperature loss via the tubing leads to an increase in energy requirement of the patient to uphold the body core temperature. These requirements cannot be met by the patient's metabolism resulting in a constant decrease of the body core temperature. To counteract this, the oxygenator (a single-use component of ECLS systems and heart-lungmachines, oxygenating the patient's blood, thus acting as lung-replacement) is equipped with a heat exchanger. This allows to heat the patient's blood via an additional heating circuit connected to heater-cooler-units. While there are devices available on the market, it is known since 2015 that these devices are contaminated with multiple bacteria, first and foremost the *Mycobacterium chimera*. The root cause being that the used devices have not been developed in regard to hygienic aspects. They are equipped with water tanks, built-in pumps and reusable tubing. This makes cleaning the devices nearly impossible. Since the hygienic risks of these devices are now known, the cleaning and disinfecting strategies are becoming more and more complex.

Another disadvantage of previous systems is that due to their architecture and method of action, they are only approved for stationary use. With increasing applications during transport and out of hospital, a mobile solution for temperature management is required. Ideally, all types of patient transportation should be considered, including transportation in rescue helicopters, aircrafts and ambulances. There is currently no approved device available on the market.

Therefore, there exists an acute clinical need for a system which overcomes these disadvantages. The object of this disclosure is to provide a temperature management system for ECMO/ECLS systems, which is developed and optimized for this specific application. First and foremost, the risk of contamination is eliminated due to its design and mode of operation.

SUMMARY

This object is achieved by a system for temperature management for patients during stationary and mobile ECLS and/or ECMO operation with the features of claim 1. Accordingly, a system for temperature management for patients in stationary and mobile ECLS and/or ECMO therapy is provided, with at least one disposable and a fluid circuit, wherein the disposable comprises at least one reservoir or bag provided with at least one supply line and a drain line, further comprising at least one pumping unit element as part of the disposable, by means of which liquid in the reservoir or bag can be pumped through the fluid circuit.

Especially, all parts of the system are completely separated from intracorporeal and extracorporeal blood circuit of the patient undergoing the ECLS and/or ECMO therapy.

For instance, the system is embodied such that in the mounted state of the system all fluid-guiding parts of the system are completely encapsulated and separated from intracorporeal and extracorporeal blood circuit of the patient undergoing the ECLS and/or ECMO therapy.

The disclosure is based on the basic aim and idea to significantly reduce the risk of contamination of the area around the patient during stationary and mobile ECLS and/or ECMO operation. Therefore, the fluid circuit, which is used to control the patient blood temperature via the oxygenators heat exchanger, is completely encapsulated. This way, especially the contamination with infectious agents, such as germs, bacteria, fungi or viruses is significantly reduced. It has been found that especially aerosols, which are generated from the temperature management fluids of existing system are spreading infectious agents. This risk has been completely eradicated with the concept of the system according to the present disclosure.

The system is used as a support to control the patients' temperature during ECLS/ECMO using the heat exchanger in the oxygenator. The user can set a desired target temperature to the temperature transporting fluid. Over time—depending on the environmental circumstances—the fluid is adjusted to target temperature. In an encapsulated circuit, the fluid is pumped to the heat exchanger where the energy is transferred to the patient or vice versa. As part of the encapsulated circuit, there is a bag located between two aluminum plates. The aluminum plates are used to adjust the temperature of the fluid in the bag.

Extracorporeal membrane oxygenation (ECMO), also known as extracorporeal life support (ECLS), is a treatment that uses a pump to circulate blood through an artificial lung back into the bloodstream. Part of this system is a heating unit, which counteracts the temperature loss to the environment and maintains the needed body temperature. Currently available heating unit devices pose high risks for patients. Due to their design, the fluid circuit contaminates easily and spreads dangerous bacteria and mycobacteria, especially by means of aerosols. Apart from other key features, the system according to the present disclosure is not directly in contact with any fluid, but only with a disposable, which encapsules the fluid for temperature management, which is what makes it hygienic, safe and easy to use and eliminates the risk of contamination. For instance, the fluid for the temperature management is filled into a sterile disposable, which eliminates the need of complex cleaning processes. ECLS treatment is inter alia a last stage treatment for patients suffering from COVID-19, where the patients' lung is supported by the oxygenator (artificial lung). It is of utmost importance that the exposure of these patients (with near respiratory failure) to additional pathogens is reduced to an absolute minimum.

The pumping function can also be performed by at least one roller pump. The circulation transports the heating fluid from the reservoir/bag—which is placed in a heating unit outside of the disposable—into the oxygenator and back. The fluid temperature in the reservoir/bag can be precisely regulated by means of regulation on the heating unit, and consequently the blood temperature of the patient can be regulated, while the risk of contamination of the patient can be avoided.

In an embodiment, the risk of contamination is eliminated by using a sterile disposable on the temperature management side and by having a separation for the temperature management fluid circuit and the fluid circuit for the oxygenator, i.e. the extracorporeal circuit of the blood oxygenator. Heat exchange is then established between the fluid circuit of the temperature management system and the fluid circuit of the ECMO/ECLS system, especially via the heat exchanger of the oxygenator. So, the surfaces or parts of the system for temperature management system are not in direct contact with the parts of the ECMO/ECLS system. The fluid of the temperature management system is filled into a sterile disposable, with no parts of the device D coming in direct contact with the fluid, eliminating the need of a complex cleaning process.

The circuit can comprise the usual components of an ECLS and/or ECMO circuit, such as a heating unit and/or an oxygenator and/or one or more heat exchanger and/or blood lines (venous line(s) and arterial line(s)) etc.

The system and the disposable are designed and set up in a way, that by regulating the heating unit, the liquid temperature in the reservoir or bag can be precisely regulated, and consequently the blood temperature of the patient can be controlled while the risk of contamination can be eliminated.

The disclosure is further based on the idea that the risk of contamination should be eliminated by design. All components in contact with the fluid are disposed of after a single use. This includes, for example, a liquid bag, which serves as a reservoir, the centrifugal pump head and the associated tubes. The complete disposable is designed as a sterile set. The permanent part of the device (i.e. the re-usable and/or permanent temperature management device)—which includes but is not limited to—a heating unit, a pump drive, an input device and necessary sensors, is not in contact with the heat-conducting fluid and thus remains free from contamination. Moreover, it is designed in a way to be easily cleaned and disinfected.

Thus, the possibility to control the patient blood temperature is provided. In contrast to available systems, the circulating fluid as well as all connected components are sterile and can be disposed of after the therapy. This way, contamination of the device, the oxygenator or the patient can be impeded.

The disposable can be configured such that it comprises all components which are in direct contact with the heat transfer fluid. This way, the used fluid for the temperature management and the heat transfer (i.e. for cooling, heating or maintaining the temperature) to the heat exchanger of e.g. the oxygenator for the ECLS/ECMO system is encapsuled during operation and after operation can be safely removed.

It is possible that the heat transfer fluid is a water based fluid, especially a physiological saline solution. A fluid for the temperature management and the heat transfer (i.e. for cooling, heating or maintaining the temperature) on the basis of water, especially by water only allows an easy to use and thermodynamically stable and advantageous use. Also, it is safe in handling. Furthermore, sterilization of the fluid is also easily possible this way.

It is especially possible that the heat transfer fluid is a physiological saline solution. This way, an easier heating because of the salt solutes in the water and the effect on the heating capacity of the water is possible. Furthermore, it enhances the safety and can be seen as an additional safety feature, as it could be infused this way in the blood of the patient and even a leakage in the heat exchanger of the oxygenator would not cause severe harm, as then sterile physiological saline solution would be infused into the blood of the patient undergoing the treatment.

Further, the system may comprise a drive, wherein a pumping unit of the system comprises at least the pumping unit element and the at least one drive, especially wherein the drive, which drives the pump head, is a part of the system and not a part of the disposable. This way the parts of the fluid mechanic driving elements are separated in a way that the part in fluid contact is part of the disposable and the drive itself can be part of a permanent device (i.e. the re-usable and/or permanent temperature management device).

The one pumping unit element can be a centrifugal pump head, which is part of the disposable.

Thus, in other words, it is possible that the pump unit consists of two parts: The centrifugal pump head which is in contact with the heat exchange fluid is part of the disposable product. The drive which is controlling the pump head is part of the permanent device. It can also be the case that the pump is an external roller pump. In that case, a pump component integrated into the disposable may not be necessary.

Additionally, it is possible that the system comprises at least one heating unit. The heating unit is a synonym for a temperature management unit, which is capable to heat, cool or maintain the temperature of the fluid used for temperature management of the heat exchanger of the oxygenator of the ECLS/ECMO system. This may for example be designed such that both sides of the bag/reservoir are heated and/or cooled by means of (a) heating element(s) in order to heat the fluid contained therein to the set target temperature. The heating unit may be not in contact with the heat transfer fluid and is thus part of the permanent device.

It is possible in a further embodiment of the disclosure that the system has a validation element configured for validating and invalidating a disposable. Thus, a multiple use and the risk of contaminating the fluid circuit can be eliminated. This can be implemented, for example, via an RFID tag integrated in the tubedisposable, which can be devalued after first use. In other words, it is possible that the system has a function for validating the disposable.

Furthermore, it can be provided that by means of a Poka-Yoke concept, incorrect insertion of the disposable product is prevented by design. A faulty operation by incorrect use is thus not possible. For example, this can be achieved that the disposable can only be inserted in one specific way into the permanent device of the system, otherwise the door of the system will not close. Without closing the door, the system cannot be started. This way, it is ensured that the system can only be started with a correct placement of the disposable within the system.

Furthermore, it can be provided that the system has an assisted and/or semi-automated and/or automated filling and/or venting function. For instance, in this case and embodiment, the system comprises a controller which is configured for an automated filling and/or venting function. For this purpose, it should be designed in a way in which the removal of air bubbles from the system at regular intervals is performed automatically or semi-automated. The function can be done in an assisted way, which is for example realized by providing guidance information via a screen or display or any optical elements or acoustical elements. Instructions for setting up the filling and/or venting of the system can be provided via e.g. the display and/or acoustical information, and this can be done step by step. Semi-automated assistance for filling and venting can be given in a way to, additionally to the assisted set up process of the system for filling and venting, the filling is assisted by semi-automatically filling the disposable, e.g. by using the drive of the pump for the filling process.

It is possible that the system comprises an operating parameter recording module, wherein this module comprises a patient data management interface by means of which data is exchangeable with a patient data management system.

Further, the system can have a synchronization interface, by means of which data is interchangeable with one or more medical devices, for instance wherein via the synchronization interface at least one command for activation or deactivation of the temperature regulating module are interchangeable.

Additionally, it is possible that the system comprises a leak detector which is configured such that leaks in the tube fluid circuit are detected automatically tube. For example, one or more sensors forming a leak detector can continuously measure the level in the reservoir bag and inform the user if the level is too low via status messages and warning signals.

Further, the system may comprise a pressure build up avoidance element, which his configured such that a pressure build up in the oxygenator is impossible. The pressure build up can be negative as well as positive pressure. So, it is possible that the system is designed in a way to avoid pressure buildup in the disposable and the oxygenator. For this purpose, centrifugal pump heads may be used, which cannot exceed the maximum permissible pressure of the disposable and the oxygenator. In case of the use of roller pumps, this may be achieved by integration of pressure relieve valves into the disposable.

It may also be provided that the system has inputs and outputs (such as a user interface) by means of which the user is able to input operating parameters, such as desired values and/or target values and/or product limits and/or maximum limits, and by means of which operating parameters can be output, and/or displayed. The system may thus have a graphical user interface, via which target values, warning limits and maximum limits can be defined by the user. By a simple and intuitive input possibility a guided user input can be made possible and operating errors can be prevented. Errors may lead to acoustic as well as to visual warning messages, which can be output via the graphical user interface. It is also conceivable that the error causes can also be described on the user interface. It is also conceivable that illustrations for troubleshooting can be displayed or concrete instructions for the next steps in the treatment process can be provided.

Furthermore, the system may be provided with an operating parameter recording module by means of which operating parameters of the system can be monitored and/or recorded. Using such a system, application data such as date, runtime, target value, actual value, warning limits, maximum limits or other operating parameters can be archived in the system in an internal memory. It is also conceivable that the operating parameter recording module is connected to an external storage system in order to archive application data there. For example, in the event of a dispute, the actual pressure processes in the system can be documented and user errors can be ruled out. In addition, such a system can be used for quality assurance.

It is also conceivable that the operating parameter recording module has a patient data management interface by means of which data can be exchanged with a patient data management system. Such a facility will make it possible to simplify data recording and data management associated with the system for patient treatment.

In addition, it may be provided that the system has a synchronization interface by means of which data can be exchanged with one or more medical devices, such as wherein at least one stop command for activating or deactivating the temperature management system can be exchanged via the synchronization interface. It is conceivable, for example, that a serial interface or other interface with a data input is provided for this purpose. By means of the interface and the corresponding signals transmitted and exchanged via it, other medical devices can turn on or switch off the temperature management system by sending a respective command. This allows the automated synchronization of processes that previously had to be performed manually. The automation of the synchronization may increase the user-friendliness and the safety of the patient.

The system may comprise a disposable and a re-usable and/or permanent temperature management device, in which the disposable is at least partially held during operation.

Furthermore, the present disclosure relates to a method for operating a system for temperature management, the method having at least the following steps:

- the fluid circuit is permanently monitored with multiple sensors,
- based on these sensor values, the actual fluid temperature is calculated,
- the heating unit is regulated based on the delta between the current temperature value and the target temperature value.

Additionally, the present disclosure relates to a disposable for a system as described above. Such a disposable comprises the features of the disposable as described in this disclosure. Further, the disposable may be configured and arranged to be used with the system and its embodiment as described in the present disclosure.

Moreover, the present disclosure relates to a temperature management device for a system as described above. Such a device comprises the features of the device as described in this disclosure.

In an embodiment, the temperature management device can be embodied as a permanent device.

The device can be configured such that the disposable can be inserted and used. All (permanent) means for temperature management and control may be provided in the device, whereas the fluid guiding parts and the parts in direct contact with the temperature management fluid are only in the disposable.

The device can be a re-usable and/or permanent temperature management device, in which the disposable is at least partially held during operation. This allows a safe and stable handling of the disposable during operation. Also, the disposable can be made of flexible materials and the permanent device can provide the necessary stability and protection to the disposable.

The heating unit can be designed, for example, as a double-sided metal surface with an attached heating foil, which heats the bag to the desired temperature with heat conducting means located therein on both sides. For example, the reservoir of the disposable can be held during operation between the metal surfaces. It is possible that the device has a main body with a door and that one metal surface is in the main body and another one in the door. This way, the temperature of the fluid within the reservoir of the disposable can be altered and changed or maintained from two sides of the reservoir, which allows a better and faster and more direct temperature control, manipulation and change.

The heating unit of the device is not in direct contact with the heat management fluid. This ensures that the surfaces of the device are less contaminated after use and simplifies the cleaning and disinfection plan of the device.

The heating unit of the device is also capable to provide cooling. Therefore, for example Peltier elements can be used for providing a cooling and heating. In an embodiment, at least one Peltier element can be used. Peltier elements allow a space reduced cooling and the overall system and construction, especially the dimensions of the permanent device may be smaller. So, the temperature in the reservoir of the disposable and thus temperature for the whole system can be regulated and controlled in two directions, i.e. the temperature can be lowered, maintained or increased.

Within the device, several Poka-Yoke means can be embodied.

Poka-Yoke is a Japanese term that means “mistake-proofing” or “inadvertent error prevention”. A poka-yoke is any mechanism in a process or design that helps an equipment operator to avoid (“yokeru”) mistakes (“poka”) defects by preventing, correcting or drawing attention to human errors as they occur.

In the context of the disclosure, this means especially that the disposable can only be placed in one specific manner into the device. By allowing only one possible placement of the disposable in the device, a fail-safe operation can be ensured.

In an embodiment, the device may provide a cavity for the reservoir of the disposable. The cavity and the reservoir may be formed such that they fit to each other. The cavity and the reservoir may be further formed asymmetrically such that the reservoir only fits in one specific way into the cavity. This, way there is a clear placement of the reservoir in the device is ensured and thus also a correct placement of the whole device.

Further the device may comprise at least one tube guide. A tube guide may be embodied as a channel and/or cavity, in which a part of the disposable may be placed. It may be designed such that the length and form of the tube guide is placed and dimensioned such that the disposable can only be placed in one specific way. This can e.g. be realized in connection with the placement of the reservoir and the attached of the driving unit element and the tube connecting the reservoir and the driving unit element. The dimension of this connecting tube can be such (e.g. embodied as the shortest tube part of the whole disposable) that only this tube part can be placed and fitted into the respective tube guide between the cavity for the reservoir and the drive.

Via such a tube guide, inter alia the safe and error-free use of the disposable product can be ensured.

The following points are or can be realized in this context:

The pump head can be used in the specially manufactured pump head holder with the drive of the pump, for example by means of bayonet closure and secured against unintentional loosening.

Via the tube guide, the tube can be guided partially within the device towards the oxygenator.

Also, it is possible that blockages or obstructions or a kinking of a tube in the disposable or somewhere in the fluid pathway may be detected. This can be done by means of pressure control and/or monitoring. Alternatively, this can be realized by implementing a monitoring routine and by detecting the power consumption of the drive unit. For example, the number of revolutions of the pump, here e.g. a centrifugal pump, can be increased. If the power uptake for this increase is not going up then this means that the transported fluid volume has not increased which does not match with the increased number of revolutions of the pump, rather the fluid in the pump head itself is only moved within the pump head but no real pumping has occurred. This is indicative for an obstruction, a blockage or a kinking of the tube or a part of the disposable. An alert will then be issued by the system.

Another possible safety feature is a blood leakage detector in the device, which is monitoring the disposable. As the disposable and all fluid guiding parts are encapsulated and completely separated by design from the blood circuit of the patient, occurrence of blood is indicative for a severe failure. In an embodiment, it can be indicative of a failure in the heat exchanger of the oxygenator. Possible blood leakage detectors can be embodied by means of at least one optical detector monitoring the fluid conduit of the system.

Furthermore, the present disclosure relates to a further method for operating a system for providing a temperature management to the water side of a heat exchanger of an oxygenator for ECLS and/or ECMO therapy, especially by using a system according to the present disclosure and/or a disposable according to the present disclosure and/or a temperature management device according to the present disclosure, the method having at least the following steps:

- establishing a fluid circuit, which is completely encapsulated and separated from intracorporeal and extracorporeal blood circuit of the patient undergoing the ECLS and/or ECMO therapy,
- providing a flow of a temperature management fluid by means of the fluid circuit to the water side of a heat exchanger.

Further details and advantages of the disclosure will now be explained with reference to an embodiment shown in more detail in the drawings. The described embodiments are to be considered in all respects only as illustrative and not restrictive, and various combinations of the recited features are included in the disclosure.

BRIEF DESCRIPTION OF THE FIGURES

It is shown in.

DETAILED DESCRIPTION

Figure 1:
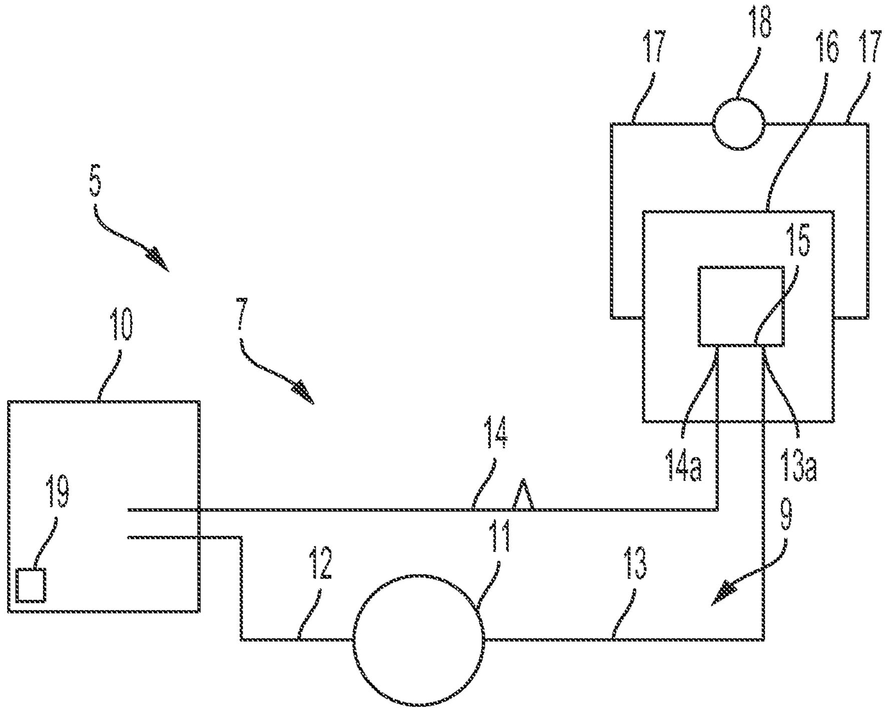
FIG. 1 a schematic overview of an embodiment of the disposable product in combination with the oxygenator.

FIG. 1 shows a schematic representation of the system 5 according to an embodiment of the present disclosure.

The system 5 comprises a disposable 7 consisting of several single components or sections.

In an embodiment, the disposable 7 comprises a bag or reservoir 10.

Further, there is a pump section 11, here in the shown embodiment the form of a centrifugal pump head 11. It is, however, possible that the pump section 11 is realized with a different pump concept and technology.

Furthermore, the disposable 7 comprises several fluid lines, i.e. fluid line 12, fluid line 13 and fluid line 14.

The fluid line 12, the fluid line 13 and the fluid line 14 can be realized in the form of a (plastic) tube or by means of a tube. For example, PVC can be used as material.

The fluid line 12 is connected with the reservoir 10 and the pump section 11.

The fluid line 13 is connected to the pump section and has at its free end a connector 13*a* for connecting with the heat exchanger 15 (such as with the water side of the heat exchanger 15) of the oxygenator 16.

The fluid line 14 is connected to the reservoir 10 and has at its free end a connector 14*a* for connecting with the heat exchanger 15 of the oxygenator 16.

The connector 13*a* can be part of a standardized tube coupling. For example, a so-called Hansen Coupling can be used. The Hansen Coupling can be a plastic component and it can be made as a disposable.

The connector 14*a* can also be part of a standardized tube coupling. For example, a so-called Hansen Coupling can be used. The Hansen Coupling can be a plastic component and it can be made as a disposable.

The heat exchanger 15 and the oxygenator 16 are not necessarily part of the system 5, but they are connectable or as shown here connected to the system 5.

The fluid line 13 is in normal operation the supply line to feed the fluid for temperature management to the heat exchanger 15 of the oxygenator 16.

The fluid line 14 is in normal operation the drain line or line back from the heat exchanger 15 to the oxygenator.

The oxygenator circuit has the components heat exchanger 15 (blood side of the heat exchanger 15), oxygenator 16, fluid lines 17 and pump 18 (also here symbolizing the patient and the reservoir).

In other words, there is a connection of the fluid system within the disposable 7 of the system 5 for temperature management via connectors 13*a* and 14*a* to the oxygenation system, having the oxygenator 16 with its heat exchanger 15 and also showing the blood circulation of the patient.

The fully assembled system 5 can be described as follows:

The disposable comprises a bag/reservoir 10, which is connected via a tube 12 to the centrifugal pump head 11. Furthermore, the fluid line 13, here a PVC tube 13 is provided and is starting from the pump head 11 for connection to the (water side of the) oxygenator 16—such as to the (water side) inlet of the heat exchanger 15 of the oxygenator 16.

Another fluid line 14 tube 14 leads from the outlet of the heat exchanger 15 of the oxygenator 16 back to the bag 10 and thus closes the circuit. In addition, a three-way stopcock may be integrated in the tube 14. This can be used for initial filling and/or for venting the system.

Furthermore, in FIG. 1, the typical prior art structure of the blood circulation through the oxygenator is shown schematically. The blood of the patient is guided with tubes 17 through the oxygenator and thereby oxygenated. Also included in the circuit are typically a pump, a blood reservoir, and the patient 18.

Also contained in the disposable is a device 19 for storing relevant data (e.g., production date, expiration date, serial number, etc.). In addition, the disposable may be invalidated after first use. Multiple use of a disposable set can thus be eliminated. For example, an RFID tag can be used for this purpose.

As fluid for the temperature management in the system 5, i.e. within the reservoir 10, the fluid lines 12, 13 and 14 and also the pump head 11 any suitable heating fluid can be used, e.g. water.

For example, also a (sterile) physiological saline solution can be used, which is also helpful to reach another level of safety.

Figure 2:
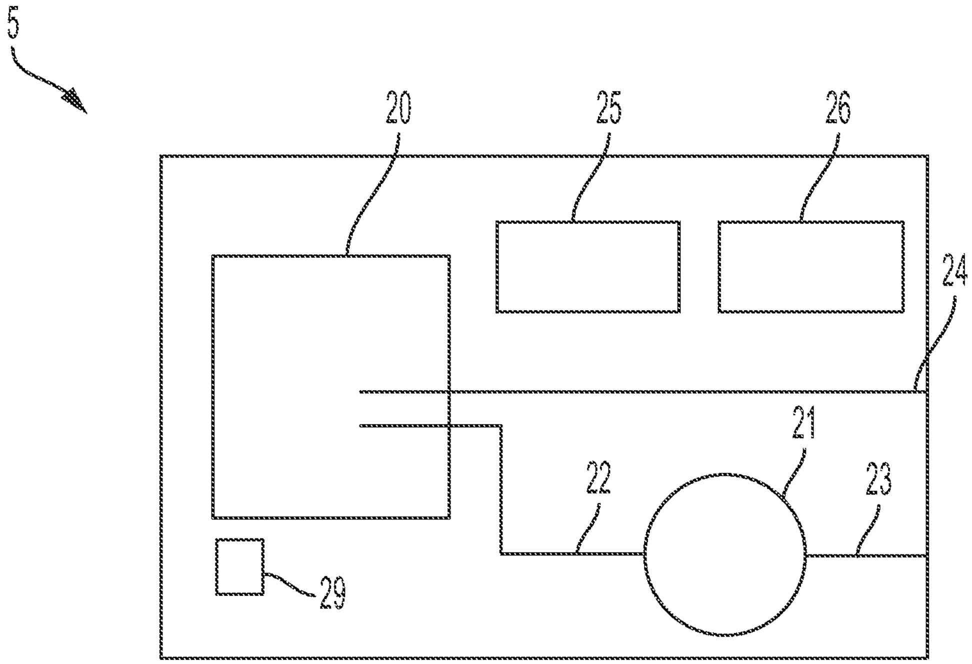
FIG. 2 a schematic overview of an embodiment of the permanent device, in which the disposable used in FIG. 1 can be inserted and operated.

FIG. 2 schematically shows the structure of a permanent device D, in which the disposable 7 can be inserted and used.

The device D is a re-usable and/or permanent temperature management device D, in which the disposable 7 is at least partially held during operation. The heating unit 20 can be designed, for example, as a double-sided metal surface with an attached heating foil and/or (a) Peltier element(s), which heats the bag to the desired temperature with heat conducting means located therein on both sides.

It is possible that the device D has a main body with a door and that one metal surface is in the main body and another one in the door.

The heating unit 20 is not in direct contact with the heat conduction.

The heating unit 20 is also capable to provide a cooling. For heating and cooling, at least one peltier element can be used.

Via a tube guide 22, the safe and error-free use of the disposable product can be ensured. Here and within the whole device, the Poka-Yoke principle can be used.

Poka-Yoke is a Japanese term that means "mistake-proofing" or "inadvertent error prevention". A poka-yoke is any mechanism in a process or design that helps an equipment operator to avoid ("yokeru") mistakes ("poka") defects by preventing, correcting or drawing attention to human errors as they occur.

In the context of the disclosure, this means especially that the disposable 7 can only be placed in one specific and safe manner into the device D.

The following points are or can be realized in this context (see also FIG. 4-6 and description below):

The pump head can be used in the specially manufactured pump head holder with the drive of the pump 21, for example by means of bayonet closure and secured against unintentional loosening. Further, in the door 30 there is a cavity 30*a* (see FIG. 5), which is designed hold the pump head 11 and which is adapted to the outer form of the pump head 11 and also only in one specific position, i.e. the correct position for the pump head 11 for operation. If the pump head 11 is not in the correct position, it will not fit into the cavity 30*a* and thus the door 30 cannot be closed.

Via the tube guide 23, the tube 13 can be guided to the oxygenator.

The tube guide 23 is fitted exactly to the length of the tube 12, which connects the reservoir 10 with the pump head 11.

The pump head 11 with its bayonet fixation mechanism must be correctly inserted and attached to the drive of the pump 21. This is also the first step, otherwise all other steps of mounting the disposable do not work correctly.

If the pump head 11 is not correctly mounted, it protrudes in such a way that the door cannot be closed. Further, there can be a counter-groove or opening or a receiving element, which receives the pump head 11 in the door of the device.

Also for the reservoir 10 there can be a cavity in the main body of the device, which is configured in a very specific and singular way to receive the reservoir 10.

The inner space of the device D is designed such that the part of the heating unit 20 in the door and the other part of the heating unit 20 in the main body 34 (cf. FIG. 4 and FIG. 5) have a defined distance between each other, which is adapted to the size and dimension of the fluid filled reservoir 10 in operation. For instance, in this fluid filled state the surfaces of the reservoir 10 are in contact with the parts/plates of the heating and/or cooling unit 20.

Additionally and/or alternatively, there may be fixation and/or positioning means such a fixation pins which are designed and configured to hold the reservoir 10. The reservoir may have specific holding openings or pin counterpart, which allow an attachment to the fixation and/or positioning pins.

In an embodiment, this cavity and the reservoir are configured asymmetrically such that the reservoir can only be inserted without mixing up the directions up and down. Only left and right orientation can be mixed up, but if this were mixed up then the pump head 11 cannot be fitted into the pump drive 21 without kinking and folding of the disposable 7 or the reservoir 10. This way, it is immediately clear that there is only one possible way of mounting the disposable into the device 10.

Without correct insertion of the reservoir 10, the disposable 7 with the tubes 12, 13, 14 and the pump head 11 to the respective receiving elements in the device D, system cannot be started.

Further, it is possible that the system can only be started, if the door of the device D is closed. As several design elements of the disposable 7 and the device D are configured such that an incorrect mounting of the disposable 7 to the device D will only lead to the fact that a part of the disposable is protruding, then the door of the device cannot be closed. This will then lead to a warning message and the system cannot start.

Via the tube guide 24, the tube of the return is fixed in the bag 10 and secured. An incorrect insertion of the tube or an unwanted kinking can be avoided.

To avoid the multiple use of a disposable set, a sensor 29, such as an NFC sensor, is integrated with the permanent device, e.g. in the door, which checks the NFC or RFID tag 19 in the disposable 7 for correctness (e.g., expiration date or prior use) and may invalidate it. Possible contamination through reuse can be made impossible. If during the set up process and the mounting of the disposable 7 to the device D the tag 19 is not recognized, the device will stop and issue an alert. No further mounting or driving of the system will be possible from this moment on.

Furthermore, all control functions and control algorithms can be integrated into a control unit 26, for example a board with integrated electronics and algorithms. This may include the control of the display, the pump and/or the heating unit, as well as the evaluation of sensors such as the NFC sensor and various temperature sensors which may be integrated in the heating unit.

In addition, the control unit 26 may comprise an operating parameter recording module, by means of which operating parameters of the system can be monitored and/or recorded.

The control unit 26 may further comprise a patient data management interface by means of which data is exchangeable with a patient data management system. For this purpose, the system may have a corresponding interface, which is formed here by a common synchronization interface. It is also conceivable that the patient data management interface communicates with other medical devices via wireless technologies.

Incidentally, it is conceivable that the control unit 26 may be formed by means of a synchronization interface. For example, a stop signal or a start command can be received by other medical devices connected to the overall system via the synchronization interface. Further, for example, a stop signal or warning signal may be sent to and/or forwarded to other medical devices in communication with the system. In addition, data can be exchanged via the synchronization interface.

Also, it is possible that blockages or obstructions or a kinking of a tube in the disposable or somewhere in the fluid pathway can be detected by the system 5, more specifically by the device D. This can be done by means of pressure control and by means of pressure sensors.

Alternatively and as implemented in the shown system 5 and device D, this is realized by implementing a monitoring routine and by detecting the power consumption of the drive unit 21.

For example, the number of revolutions of the pump, here e.g. a centrifugal pump, can be increased.

If the power uptake for this increase is not going up then this means that the transported and pumped fluid volume is not increased and does not match with the increased number of revolutions of the pump unit 21, rather the fluid in the pump head 11 itself is only moved within the pump head 11 but no real pumping happens anymore.

This is indicative for an obstruction, a blockage or a kinking of one of the tubes 12, 13, 14 or a part of the disposable 7.

An alert will then be issued by the system 5 and the device D, e.g. via the display 25 of the device D.

Another possible safety feature is a blood leakage detector in the device, which is monitoring the disposable. As the disposable and all fluid guiding parts are encapsulated and completely separated by design from the blood circuit of the patient, occurrence of blood is indicative for a severe failure. In an embodiment, it can be indicative of a failure in the heat exchanger of the oxygenator. Possible blood leakage detectors can be embodied by means of at least one optical detector monitoring the fluid conduit of the system.

By way of example, the following routine is conceivable for inserting the disposable set from FIG. 1 into the permanent device from FIG. 2.

The system 5 and the device D have an assisted and semi-automated filling and/or venting function. For instance, in this case and embodiment, the system comprises a controller which is configured for guided an automated filling and/or venting function. Guidance information is provided via a screen or display or any optical elements or acoustical elements. Instructions for setting up the filling and/or venting of the system are provided via e.g. the display and/or acoustical information, and this can be done step by step. Semi-automated assistance for filling and venting can be done that additionally to the assisted set up process of the system for filling and venting the filling is assisted by semi-automatically filling the disposable, e.g. by using the drive of the pump for the filling process.

The set up in general works as follows:

1. Insert the centrifugal pump head 11 in the pump head fixture 21 and engage by using the bayonet mechanism of the fixture
2. Insert the bag 10 in the fixtures of the heating unit 20
3. Guide the tubing 12 along the predetermined tubing guide 22
4. Guide the tubing 13 along the predetermined tubing guide 23
5. Guide the tubing 14 along the predetermined tubing guide 24
6. Connect the tubing 13 to the inlet of the heat exchanger 15 of the oxygenator 16 via the Hansen connectors 13*a*
7. Connect the tubing 14 to the outlet of the heat exchanger 15 of the oxygenator 16 via the Hansen connectors 14*a*
8. Fill the disposable with sterile fluid (e.g. water or NaCl) via the three-way-stopcock attached to the bag 10
9. Perform the semi-automated priming process to remove all air from the disposable
10. Close the three-way-stopcock and insert it into the designated insert in the heating unit 20
11. If all steps have been performed correctly, the operator is now able to easily and smoothly close and lock the door and start the device.

Figure 3:
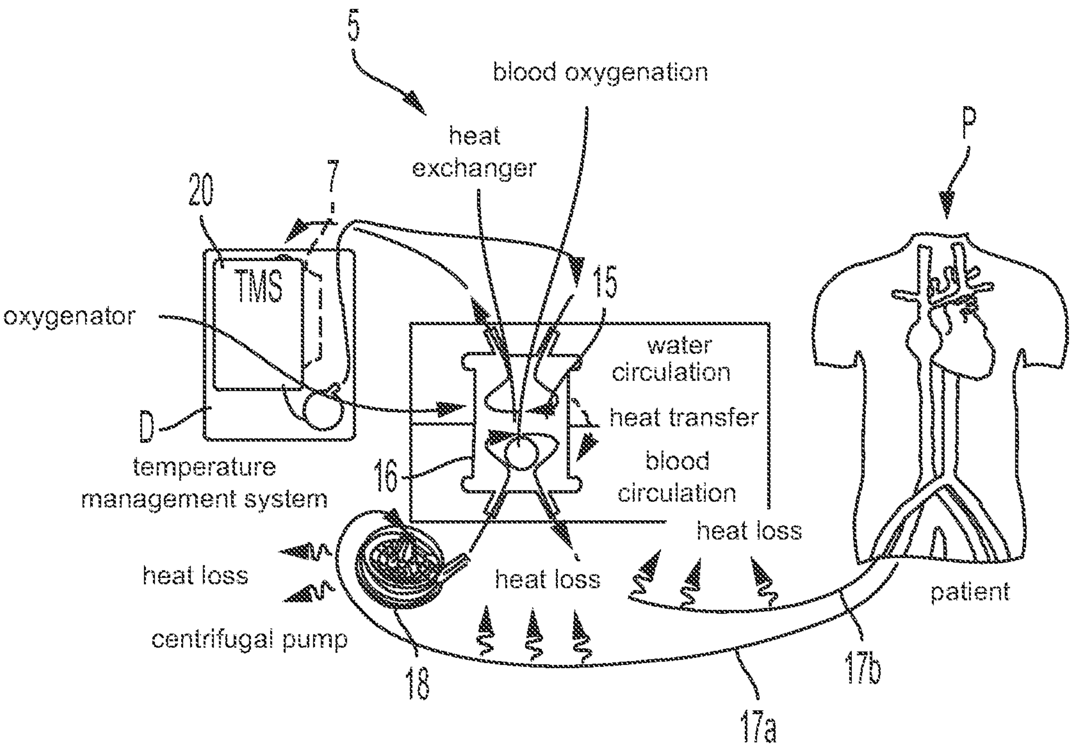
FIG. 3 a further schematic overview of a possible embodiment of the system, with a respective disposable and an oxygenator in operation and connected to the patient.

FIG. 3 shows a further schematic overview of the possible embodiment of the system 5 as shown in FIG. 1 und FIG. 2, with a respective disposable 7 and the oxygenator 16 in operation and connected to the patient P. As can be further seen in FIG. 3, the temperature management system 5 is connected to the heat exchanger 16 of the oxygenator 16.

The possible method of the system 5 with the respective disposable 7 and the device D can be as follows:

The system 5 with the device D and the disposable 7 is used as a support to control the patients' temperature during ECLS/ECMO using the heat exchanger 15 in the oxygenator 16. The user can set a desired target temperature to the temperature transporting fluid (e.g. water). Over time—depending on the environmental circumstances—the fluid is adjusted to target temperature. In the encapsulated circuit of the system 5, the fluid is pumped with the pump drive 21 to the heat exchanger 15 where the function of the heat exchanger transfers the temperature to the patient P.

On the blood side of the oxygenator 16, the blood is pumped by means of the centrifugal pump 18 via the line 17 (arterial line 17*a*) to the oxygenator 16, is there controlled and adjusted in its temperature by means of the heat exchanger 15 and pumped back to the patient P via venous line 17*b*.

Figure 4:
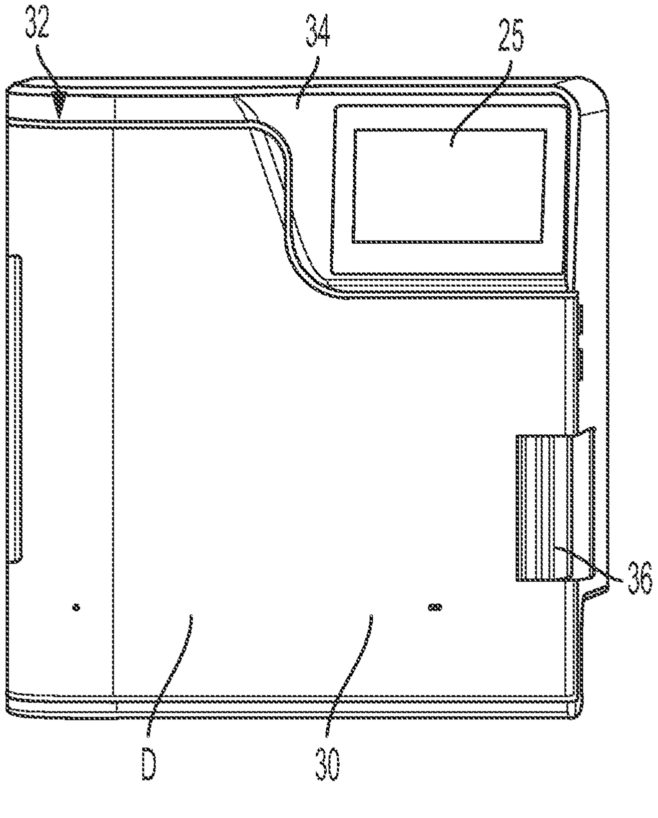
FIG. 4 a front view of an embodiment of the system according to the present disclosure with a closed door.

FIG. 4 shows a front view of an embodiment of the system 5 and the device D according to the present disclosure, which is also shown schematically in FIG. 1 and FIG. 2. Here, the front door of the device D is closed.

The device D has a front door 30, hinges 32, a main body 34 and a door handle 36.

By means of the hinges 32, the door 30 can be pivoted relatively to the main body 34.

The door 30 is not completely covering the front surface of the main body 34, but leaves the space around the display 25 completely free, so that the display 25 is visible during operation and with a closed front door 30.

The display 25 can be a touchscreen as shown here. On the display, the graphical user interface (GUI) will be displayed.

The graphical user interface shows the setup routine visually in a step by step process.

After finishing the setup routine, the user can set the target temperature in a range from 34° C. to 38.5° C. and start the therapy.

The status of the device is constantly displayed.

To increase the usability, the graphical user interface can alternatively be adjusted with navigation buttons on the bottom side of the display.

To protect the device from unwanted changes in the settings, a lockscreen is available.

The display lock protects from unwanted commands caused for example by splashing fluids or during cleaning of the surface.

Figure 5:
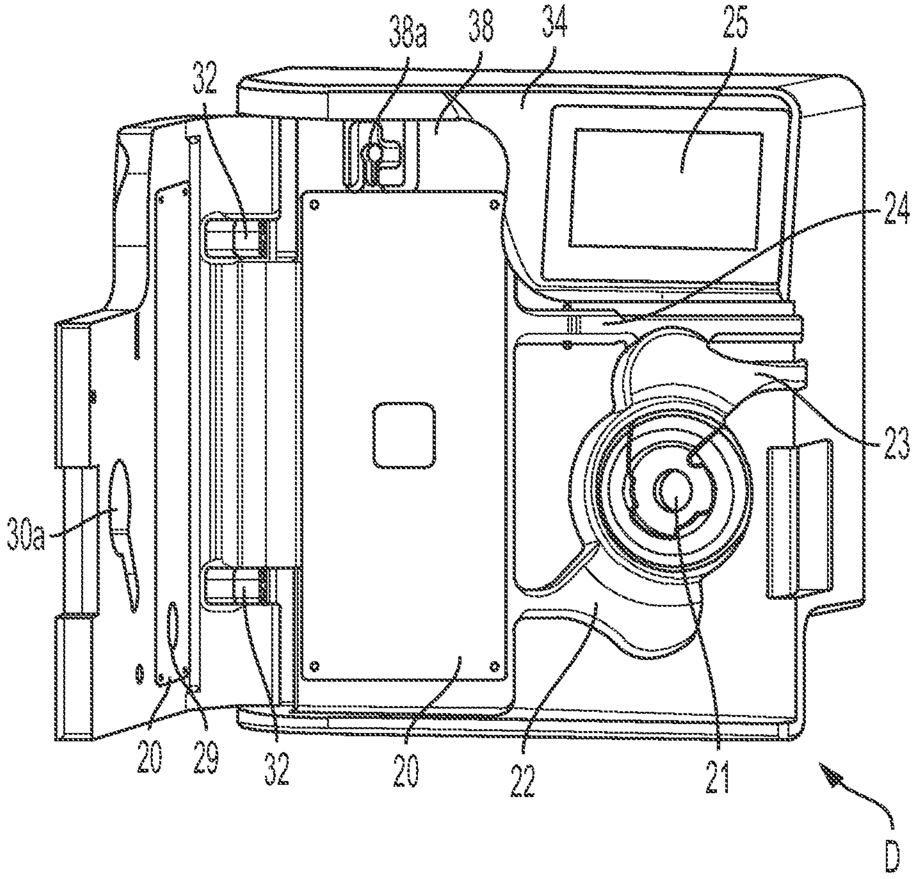
FIG. 5 a front view of the system according to FIG. 4 with an open door without disposable.

FIG. 5 shows a front view of the system 5 according to FIG. 4 with an open door without disposable.

As can be seen, in the door there is a heating unit 20 and also a sensor unit 29.

The heating unit 20 is embodied as an aluminum plate. It is designed to provide a heating functionality only.

The sensor unit 29 is capable to monitor the temperature.

Also, there can be a further sensor to check the NFC tag of the disposable. This sensor can be placed within the main body 34, e.g. behind one of the parts of the heating unit 20.

There is another heating unit 20 located in a cavity 38 of the main body 34, also embodied as aluminum plate. Here, a heating and also a cooling function can be provided.

From the cavity 38, the tube guide 22 is formed as a channel in the surface of the main body 34 and leads to the pump drive 21.

Also the other tube guides 23 and 24 are formed as a channel in the surface of the main body 34.

One aluminum plate is in the door 30 of the device D and one in the main body 34.

Figure 6:
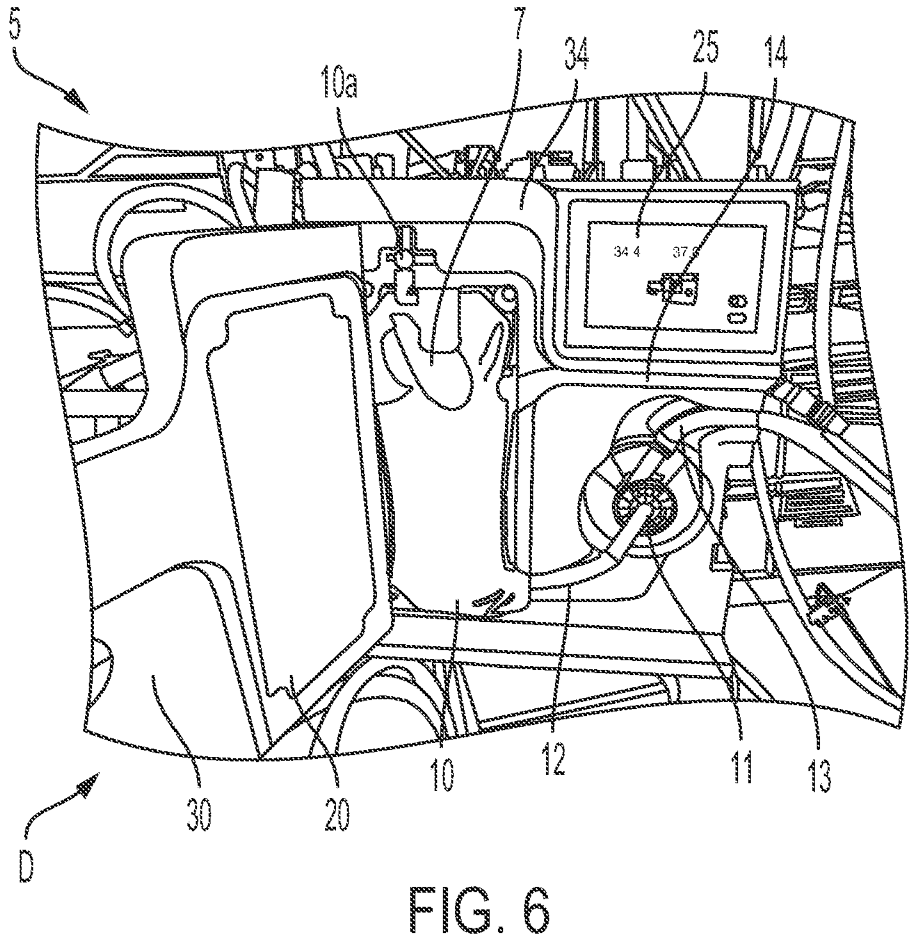
FIG. 6 a front view of the system according to FIG. 4 with an open door with disposable.

FIG. 6 shows a front view of the system 5 according to FIG. 4 with an open door 30 of the device D, with the disposable 7 being correctly inserted into the cavity 38 and the tubes guides 22, 23 and 24.

As can be seen, there is a stopcock 10*a* attached to the reservoir 10.

This stopcock 10*a* or 3-way valve 10*a* can also be connected to the reservoir 10.

The stopcock 10*a* has one opening being connected to the reservoir 10, and two free ends, i.e. two free Luer-connectors. One Luer connector can be used for fluid supply during filling, and one for air removal during filling.

The stopcock 10*a* can be placed in a specific stopcock cavity 38*a* (see FIG. 5). It is possible that the stopcock cavity is designed such that the stopcock is correctly and completely received within the stopcock cavity only when the stopcock is correctly closed (i.e. the two free Luer-connectors are closed) and the reservoir is no longer open.

Figure 7:
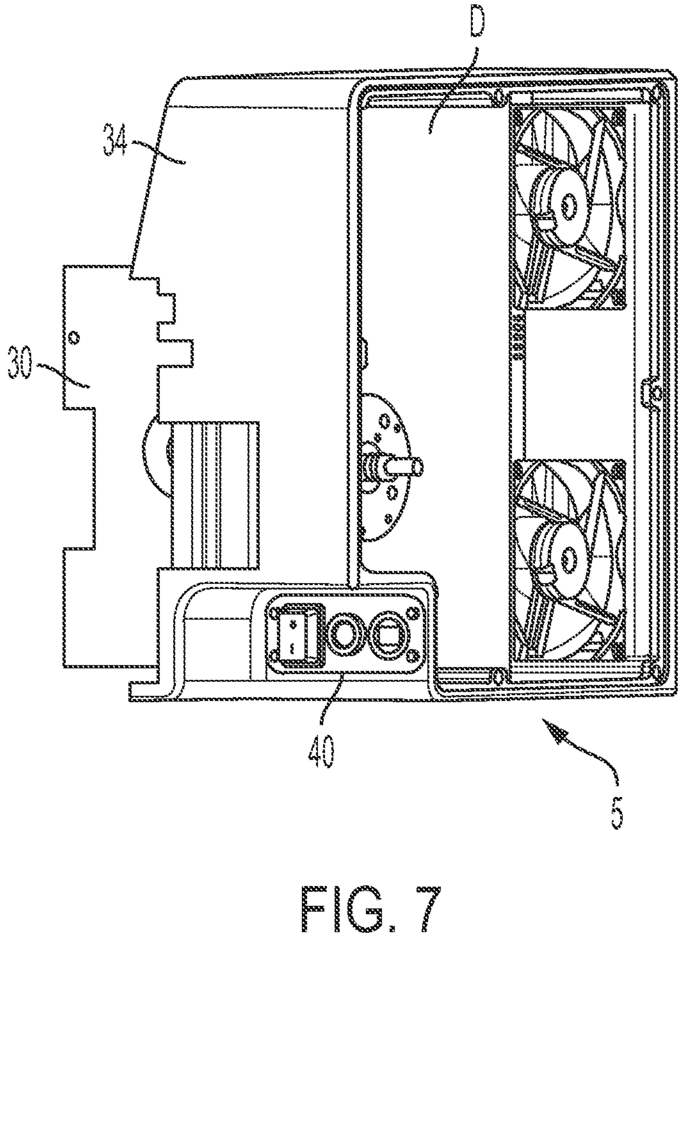
FIG. 7 a rear view of the system with closed back wall.
Figure 8:
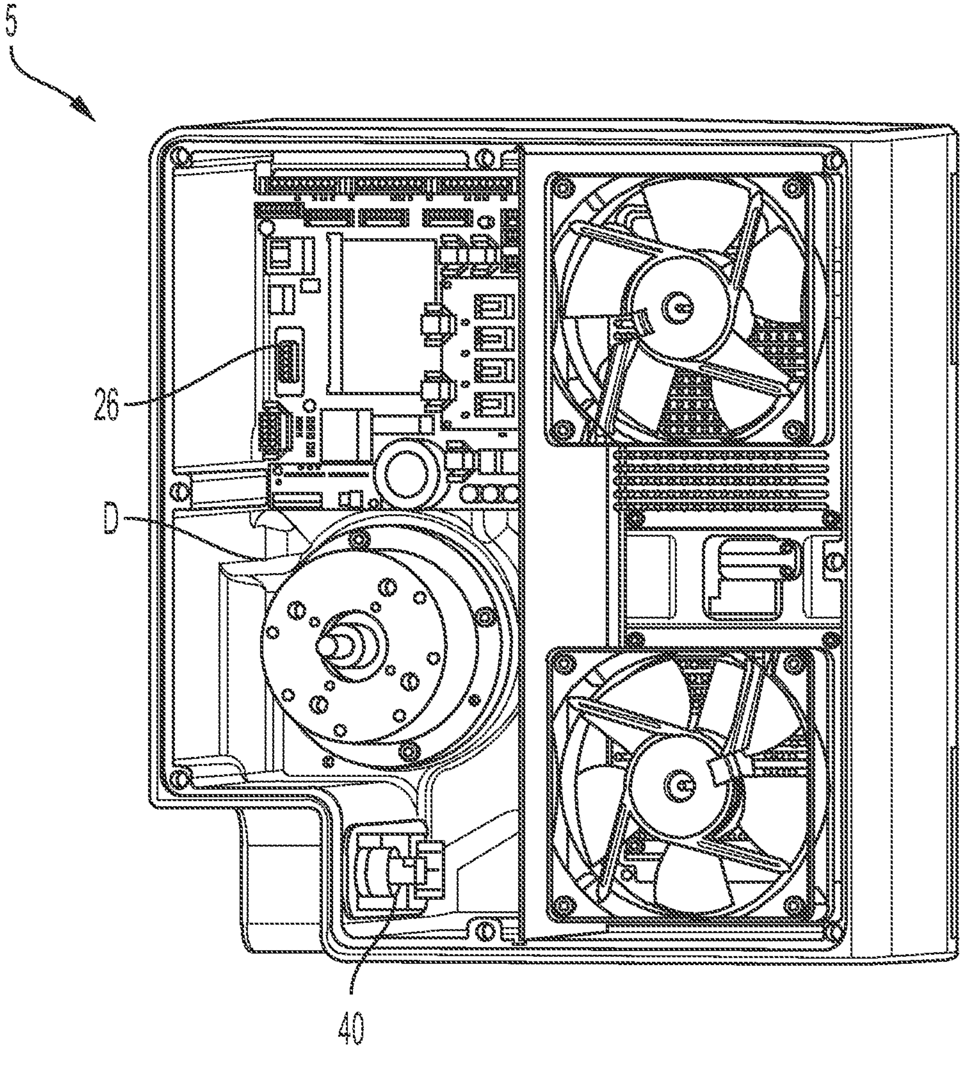
FIG. 8 a rear view of the system with open back wall.

FIG. 7 and FIG. 8 show a rear view of the system 5.

In FIG. 7 the device D is shown with the opened door 30 and the main body 34.

In FIG. 8, the system 5 with an open back wall is shown. As can be seen here, the control unit 26 and its electronics with a printed circuit board (PCB) are accessible from the rear part of the device D.

The device D has a 24V power supply 40 with an external DCDC converter in this embodiment.

Figure 9:
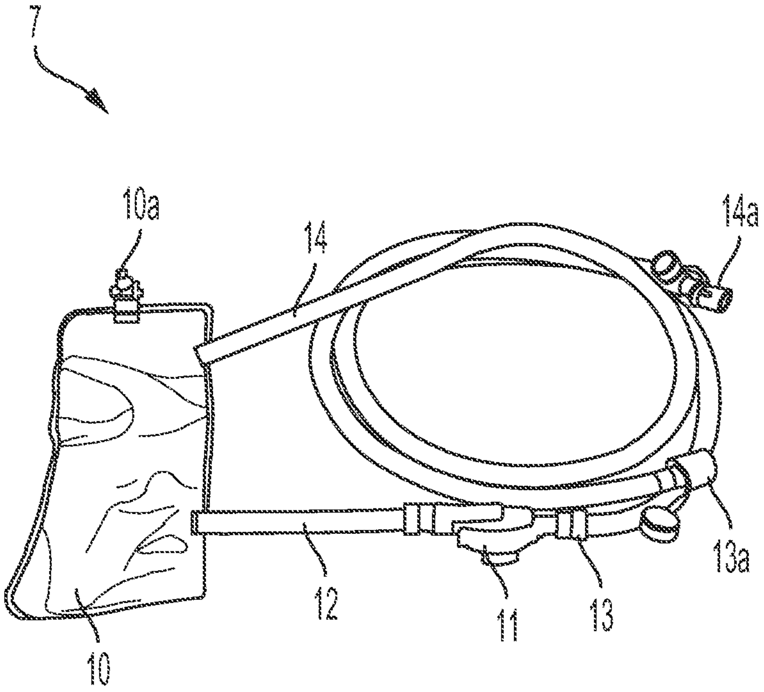
FIG. 9 the disposable for the system as shown in FIG. 1 to FIG. 8.

FIG. 9 shows the disposable 7 with the reservoir 10, the stopcock 10*a*, the fluid line 12, the centrifugal pump head 11, the fluid line 13, the Hansen connector 13*a* (Hansen Coupling 13*a*), the fluid line 14 with the Hansen connector 14*a* (Hansen Coupling 14*a*).

Figure 10:
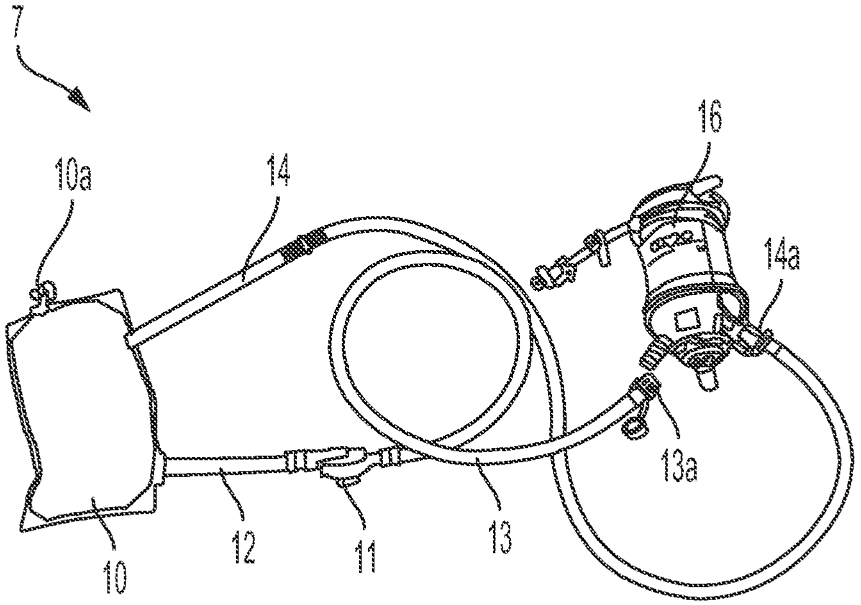
FIG. 10 shows the disposable connected to the heat exchanger of the oxygenator.

FIG. 10 shows the disposable 7 with all the elements as shown in FIG. 9 connected to the heat exchanger 15 of the oxygenator 16.

The function of the system 5 can be described as follows:

As part of the encapsulated circuit, there is a bag 10, i.e. the reservoir 10 located between two aluminum plates forming the two heating units 20. The aluminum plates are used to adjust the temperature of the fluid in the bag 10.

There are three different modes available. Before starting a new therapy, the user is guided to set up the disposable in the device. Once the setup is finished, the user sets the desired target temperature which leads to either heating or cooling.

In the setup routine, the user visually guided by the display to step by step set up a new disposable set in the device D. The main steps, which are displayed, are:

1. Insert the pump head
2. Insert the bag
3. Connect to Oxygenator
4. Fill with fluid and remove air
5. Close door (locks disposable)

Once the disposable set is installed correctly, the user can access the main menu to adjust the desired target temperature and start the therapy.

In a typical use case, the intention of the operator is to compensate the lost temperature to the environment through the extracorporeal tubes. The operator uses the graphical user interface on the display 25 to set the desired temperature, e.g. 38° C. As a result the two aluminum plates will (in the door 30 and also in the main housing 34) heat up to transfer heat to the fluid. To minimize risk to patient and operator, the heating plates will not be heated to more than a user-defined or pre-defined maximum value, such as e.g. 45° C. The permanent target of the heating plates are to reach the target temperature in the fluid. Depending on the environmental circumstances, the time until the target temperature is reached can differ.

In another use case, the intention of the operator is to gently cool down the patient, possibly in case when he shows fever. The operator uses the graphical user interface on the display 25 to set the desired temperature, e.g. 35° C. As a result the aluminum plate in the main body 34 will cool down to remove temperature from the fluid. The aluminum plate in the door 30 will not operate in that time and remains on normal temperature. The permanent target of the cooling plate is to reach the target temperature in the fluid. Depending on the environmental circumstances, the time until the target temperature is reached can differ.

The safety features and advantages of system 5 and the device D can be summarized as follows:

The main feature of the device is that the water circulation is completely detached and separated from the device D. This is realized by the usage of a sterile disposable. Heating and pumping of the heating fluid as well as temperature- and flow-control are handled non-invasively. Thus, the contamination of the device can be reduced to a minimum and a sterile and safe patient blood temperature management is guaranteed.

The disposable 7 and the disposable integrating interface in the device D are designed to provide maximum safety in terms of safety and usability.

All safety features and measures to archive maximum safety in this specific regards are listed here:

- The pumphead is detected by the pump. If the pump head is removed, this will be detected and operation is not possible.
- The pumphead must be locked with bayonet mechanism. There is no operation possible when the pumphead is inserted but not locked, because of multiple reasons:
- The door can physically not be closed if the pump head is not turned all the way to lock position. The tube does not fit the tube guide yet the door cannot be closed.
- All tubes in the device are guided. If a tube is not correctly installed in the guide, the tube will block the door from being closed. As a result no operation is possible.
- The bag mount has four fixation points defining the exact location of the bag.
- There is an NFC tag located on the bag. If the bag does not have the correct position, the NFC tag is not detected hence there is no operation possible.
- To increase comfort in usability for the operator, there is a three-way-stopcock located on the top side of the bag. It serves two purposes. It allows the operator to comfortably fill the bag while letting the operator remove air at the same time only by turning the handle of the three-way-stopcock.
- The three-way-stopcock can only be placed in the housing in a way that it is closed. If the handle is rotated in a way that opens an unwanted outlet, it blocks the door from being closed, hence no operation is possible.
- There is a water level detector installed to ensure there is sufficient water in the disposable bag. Potential leaks will case a drop in the water level. The water level sensor detects this during the setup routine or during therapy so that the device D can act accordingly.
- The status of the door is automatically detected. As long as the door is open, the operator cannot start therapy.
- Once the door is closed, all sensitive parts of the disposable are covered so that they cannot accidently be manipulated. The door forces all disposable elements to stay in place.
- Between the device D and the oxygenator the tubes are not guided and can be accessed.
- An integrated occlusion detection notifies the operator about a potential hazardous situation caused by an occlusion or a kink in the tube, see above description in connection with the monitoring of the power consumption. There is an alarm if during therapy the fluid flow can be stopped so that the operator can react immediately.

Summarizing, it can be said that to solve the main problems with current devices on the market by design, the heating fluid in the system 5 is encapsulated in a sterile disposable set 7. For every therapy, a new clean and sterile disposable set must be used. With this, all components touching the fluid will be disposed after usage. This includes the tubes (i.e. fluid lines 12, 13, 14), the bag 10 (reservoir 10), the pump-head 11 and the connectors of the disposable set 7. This design enables the user to eliminate the risk of contamination and the need for a complex cleaning process of the device D.

FIGS. 1-10 show example configurations with relative positioning of the various components. If shown directly contacting each other, or directly coupled, then such elements may be referred to as directly contacting or directly coupled, respectively, at least in one example. Similarly, elements shown contiguous or adjacent to one another may be contiguous or adjacent to each other, respectively, at least in one example. As an example, components laying in face-sharing contact with each other may be referred to as in face-sharing contact. As another example, elements positioned apart from each other with only a space there-between and no other components may be referred to as such, in at least one example. As yet another example, elements shown above/below one another, at opposite sides to one another, or to the left/right of one another may be referred to as such, relative to one another. Further, as shown in the figures, a topmost element or point of element may be referred to as a "top" of the component and a bottommost element or point of the element may be referred to as a "bottom" of the component, in at least one example. FIGS. 4-10 are drawn to scale.

As used herein, top/bottom, upper/lower, above/below, may be relative to a vertical axis of the figures and used to describe positioning of elements of the figures relative to one another. As such, elements shown above other elements are positioned vertically above the other elements, in one example. As yet another example, shapes of the elements depicted within the figures may be referred to as having those shapes (e.g., such as being circular, straight, planar, curved, rounded, chamfered, angled, or the like). Further, elements shown intersecting one another may be referred to as intersecting elements or intersecting one another, in at least one example. Further still, an element shown within another element or shown outside of another element may be referred as such, in one example.

The following claims particularly point out certain combinations and sub-combinations regarded as novel and non-obvious. These claims may refer to "an" element or "a first" element or the equivalent thereof. Such claims should be understood to include incorporation of one or more such elements, neither requiring nor excluding two or more such elements. Other combinations and sub-combinations of the disclosed features, functions, elements, and/or properties may be claimed through amendment of the present claims or through presentation of new claims in this or a related application. Such claims, whether broader, narrower, equal, or different in scope to the original claims, also are regarded as included within the subject matter of the present disclosure.

REFERENCE NUMBERS

5 System
7 Disposable
9 Fluid Circuit
10 Bag/reservoir
10*a* stopcock
11 Centrifugal pump head
12 Tube to centrifugal pump head

13 Tube to oxygenator
13*a* Connector
14 Tube from oxygenator with three-way spigot
14*a* Connector
15 Heat exchanger of the oxygenator
16 Oxygenator
17 Blood-bearing tubes
17*a* Arterial Line
17*b* Venous Line
18 Pump, blood reservoir and patient
19 Device for storing relevant data
20 Heating unit
21 Pump drive
22 Tube guide to centrifugal pump head
23 Tube guide to oxygenator
24 Tube guide from the oxygenator with three-way spigot
25 Display
26 Control unit
29 Sensor for reading the data in the disposable set
30 Door
32 Hinge
34 Main Body
36 Door handle
38 Cavity
40 Power Supply
D Temperature Management Device
P Patient

The invention claimed is:

1. A system for temperature management for a patient in stationary and mobile ECLS and/or ECMO therapy, comprising:

at least one disposable, wherein the at least one disposable comprises at least one reservoir or bag provided with at least one supply line and a drain line, further comprising at least one pumping unit element as part of the at least one disposable configured to pump heat transfer fluid in the at least one reservoir or bag through a fluid circuit that includes the at least one reservoir or bag, the at least one supply line, the drain line, and a heat exchanger of an oxygenator for the mobile ECLS and/or ECMO therapy, such that the at least one pumping unit element and the at least one supply line are downstream of the at least one reservoir or bag and upstream of the drain line; the at least one reservoir or bag, the at least one pumping unit element, and the at least one supply line are upstream of the heat exchanger; and the drain line is downstream of the heat exchanger, and a temperature management device configured to house the at least one disposable, the temperature management device including a leak detector which is configured such that leaks in the fluid circuit are detected automatically, wherein, in a mounted state of the system, all fluid-guiding parts of the system are completely encapsulated and separated from intracorporeal and extracorporeal blood circuit of the patient undergoing the mobile ECLS and/or ECMO therapy.

2. The system according to claim 1, wherein the disposable is configured such that it comprises all components of the system which are configured to be in direct contact with the heat transfer fluid, and wherein the temperature management device comprises a main body including a door configured to open and close to provide access to a cavity in the main body, the cavity configured to accommodate the at least one reservoir or bag.

3. The system according to claim 2, wherein the heat transfer fluid is a water based fluid, and wherein the cavity and the at least one reservoir or bag each have an asymmetric shape.

4. The system according to claim 2, wherein the system further comprises at least one drive, wherein a pumping unit of the system comprises at least the pumping unit element and the at least one drive, and wherein the at least one drive is a part of the temperature regulating device and not a part of the disposable.

5. The system according to claim 4, wherein the at least one pumping unit element is a centrifugal pump head, which is part of the disposable, and wherein the door is configured to accommodate the pump head.

6. The system according to claim 5, wherein the temperature management device comprises at least one heating and/or cooling unit, and wherein at least a portion of the at least one heating and/or cooling unit is accommodated in the door.

7. The system according to claim 1, wherein the system comprises at least one validation element configured for validating and invalidating the disposable.

8. The system according to claim 1, wherein the system comprises a controller, which is configured for an assisted and/or semi-automated and/or an automated filling and/or venting function.

9. The system according to claim 1, wherein the system comprises an operating parameter recording module.

10. The system according to claim 1, wherein the system has a synchronization interface, by which data is interchangeable with one or more medical devices.

11. The system according to claim 1, wherein the at least one pumping unit element comprises a pump head fluidly coupled to the reservoir or bag via the at least one supply line.

12. The system according to claim 1, wherein the system comprises a pressure build up avoidance element, which his configured such that a pressure buildup in an oxygenator is impossible.

13. The system according to claim 1, wherein the leak detector comprises one or more sensors configured to continuously measure a level in the reservoir or bag and inform a user if the level is too low via status messages and warning signals, the one or more sensors comprising one or more of a water level sensor and an optical sensor configured to detect blood in the heat transfer fluid.

14. The system according to claim 9, wherein the operating parameter recording module comprises a patient data management interface by which data is exchangeable with a patient data management system.

15. A method for providing a temperature management to a water side of a heat exchanger of an oxygenator for ECLS and/or ECMO therapy by using a system including a disposable and a temperature management device configured to house the disposable, wherein the disposable comprises a reservoir or bag provided with at least one supply line and a drain line and a pumping unit element configured to pump heat transfer fluid in the reservoir or bag through a fluid circuit, the method comprising:

establishing the fluid circuit, which is completely encapsulated and separated from intracorporeal and extracorporeal blood circuit of a patient undergoing the ECLS and/or ECMO therapy, wherein establishing the fluid circuit comprises connecting the at least one supply line and the drain line to the water side of the heat exchanger, and providing a flow of the heat transfer fluid by the fluid circuit from the reservoir or bag to the water side of the heat exchanger via the pumping unit element.

16. A system for temperature management for a patient in stationary and mobile ECLS and/or ECMO therapy, comprising:

at least one disposable comprising a reservoir or bag provided with at least one supply line and a drain line and a pump head configured to pump heat transfer fluid in the reservoir or bag through a fluid circuit that includes the at least one reservoir or bag, the at least one supply line, the drain line, and a heat exchanger of an oxygenator for the mobile ECLS and/or ECMO therapy, wherein the at least one supply line includes a first supply line configured to couple the reservoir or bag to the pump head and a second supply line configured to couple the pump head to the heat exchanger, and wherein the drain line is configured to couple the reservoir or bag to the heat exchanger to thereby form the fluid circuit, such that the pump head, the first supply line, and the second supply line are downstream of the at least one reservoir or bag and upstream of the drain line; the at least one reservoir or bag, the pump head, the first supply line, and the second supply line are upstream of the heat exchanger; and the drain line is downstream of the heat exchanger, and a temperature management device configured to house the at least one disposable, the temperature management device comprising a leak detector which is configured such that leaks in the fluid circuit are detected automatically, a main body including a door configured to open and close to provide access to a first cavity in the main body, and a heating unit, wherein the door includes a second cavity that is configured to accommodate the pump head, wherein a portion of the heating unit is accommodated in the door, and wherein, in a mounted state of the system where the disposable is housed in the temperature management device, all fluid-guiding parts of the system are completely encapsulated and separated from intracorporeal and extracorporeal blood circuit of the patient undergoing the mobile ECLS and/or ECMO therapy.

17. The system of claim 16, wherein the first cavity is configured to accommodate the reservoir or bag, and wherein the first cavity and the reservoir or bag each have an asymmetric shape.

18. The system of claim 16, wherein the heating unit includes a first plate positioned in the main body and a second plate positioned in the door, wherein the temperature management device further includes a first tube guide and a second tube guide, and wherein, in the mounted state of the system where the disposable is housed in the temperature management device, the first supply line is housed in the first tube guide and fully contained in the temperature management device and the drain line is partially housed in the second tube guide.

* * * * *